US012594310B2

(12) United States Patent
Jeong et al.

(10) Patent No.: US 12,594,310 B2
(45) Date of Patent: Apr. 7, 2026

(54) COMPOSITION COMPRISING LACTIC ACID BACTERIA DERIVED FROM GREEN TEA FOR IMPROVING LIVER FUNCTION

(71) Applicant: AMOREPACIFIC CORPORATION, Seoul (KR)

(72) Inventors: Hyun Woo Jeong, Yongin-si (KR); Donghyun Cho, Yongin-si (KR); Wanki Kim, Yongin-si (KR); Jong Hwa Roh, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 451 days.

(21) Appl. No.: 18/313,465

(22) Filed: May 8, 2023

(65) Prior Publication Data

US 2023/0372417 A1     Nov. 23, 2023

(30) Foreign Application Priority Data

May 18, 2022     (KR) ........................ 10-2022-0060804

(51) Int. Cl.
*A61K 35/747*     (2015.01)
*A61P 1/16*     (2006.01)

(52) U.S. Cl.
CPC .............. *A61K 35/747* (2013.01); *A61P 1/16* (2018.01); *A23V 2400/169* (2023.08)

(58) Field of Classification Search
CPC .......... A61P 1/16; A61K 35/747; A61K 36/82
See application file for complete search history.

(56) References Cited

U.S. PATENT DOCUMENTS

| | | | |
|---|---|---|---|
| 2020/0254033 A1 | 8/2020 | Seo et al. | |
| 2023/0201282 A1 | 6/2023 | Lee et al. | |

FOREIGN PATENT DOCUMENTS

| | | |
|---|---|---|
| CN | 108641988 A | 10/2018 |
| CN | 109182191 B | 8/2021 |
| CN | 113786419 A | 12/2021 |
| KR | 10-2013-0000003 | 1/2013 |
| KR | 10-2163551 B1 | 10/2020 |

OTHER PUBLICATIONS

John's Hopkins medicine, Health—5 Ways to Be Kind to Your Liver; https://www.hopkinsmedicine.org/health/wellness-and-prevention/5-ways-to-be-kind-to-your-liver; accessed on Sep. 27, 2025 (Year: 2025).*
Jung et al., "Effect of Oral Intake of Lactiplantibacillus plantarum APsulloc 331261 (GTB1TM) on Diarrhea-Predominant Irritable Bowel Syndrome: A Randomized, Double-Blind, Placebo-Controlled Study", Nutrients, 2022, vol. 14, No. 10, pp. 1-16.
Zhao et al., "Lactobacillus plantarum NA136 improves the non-alcoholic fatty liver disease by modulating the AMPK/Nrf2 pathway", Applied Microbiology and Biotechnology, 2019, vol. 103, No. 14, pp. 5843-5850.
Fang et al., "Protective effects of Lactobacillus plantarum against chronic alcohol-induced liver injury in the murine model", Applied Microbiology and Biotechnology, 2019, vol. 103, No. 20, pp. 8597-8608.
Eun-Jung Park et al., "Beneficial Effects of Lactobacillus plantarum Strains on Non-Alcoholic Fatty Liver Disease in High Fat/High Fructose Diet-Fed Rats", Nutrients, 2020, vol. 12, No. 2, pp. 1-16.
Chuan Li et al., "Lactobacillus plantarum NCU116 improves liver function, oxidative stress and lipid metabolism in rats with high fat diet induced non-alcoholic fatty liver disease", Food & Function, 2014, vol. 5, No. 12, pp. 3216-3223.
Hyun Woo Jeong et al., "Heat-Killed Lactiplantibacillus plantarum APSulloc 331261 Enhances Lipid Catabolism Through AMPK Activation in HepG2 Cells", Food Supplements and Biomaterials for Health, 2022, vol. 2, No. 4, pp. 1-17.
Extended European search report issued in 23170317.4 dated Oct. 12, 2023, 14 pgs.

* cited by examiner

*Primary Examiner* — Brian Gangle
*Assistant Examiner* — Lakia J Jackson-Tongue
(74) *Attorney, Agent, or Firm* — Rothwell, Figg, Ernst & Manbeck, P.C.

(57) ABSTRACT

A method for improving hepatic function, including administering an effective amount of a composition including a green tea-derived *Lactiplantibacillus plantarum* strain; a culture of the strain; a lysate of the strain; an extract of the strain; an extract of the culture; or an extract of the lysate to a subject in need thereof is disclosed in the specification.

6 Claims, 6 Drawing Sheets

A

B

RFP Fluorescence

COMPOSITION COMPRISING LACTIC ACID BACTERIA DERIVED FROM GREEN TEA FOR IMPROVING LIVER FUNCTION

CROSS REFERENCE TO RELATED APPLICATION

The present application claims priority to Korean Patent Application No. 10-2022-0060804, filed May 18, 2022, the entire contents of which are hereby incorporated by reference.

BACKGROUND OF THE INVENTION

Field of the Invention

The disclosure relates to a composition for improving hepatic function.

Description of the Related Art

The liver is the largest internal organ in the human body and the main function of the liver is to process various materials introduced from outside the body or produced in the body, and to synthesize and supply important materials. Also, there are several proteins in the blood that play an important role in our body, and about 90% of the proteins in the blood are produced in the liver. Further, the liver has detoxifying function, and acts as an immune organ. Various drugs and hazardous materials that enter the human body are converted into less hazardous ones, which are secreted out of the body through urine or bile. Still further, Kupffer cells, immune cells in the liver, function to phagocytose and degrade any bacteria, toxins, or foreign substances that come from outside the body and then remove them from the body. Also, the liver has the remarkable regenerative power, so that, even after up to 75% partial hepatectomy, the liver restores its full functionality and size within 4 to 6 months.

Since the liver performs a variety of important functions, various problems arise when hepatic function deteriorates. In particular, a fatty liver disease, which is easily developed in modern people who consume excessive amounts of alcohol, is one of the representative liver diseases. Most of the fat accumulated in the fatty liver is triglyceride, and fatty liver can be largely divided into alcoholic fatty liver caused by excessive alcohol consumption and non-alcoholic fatty liver caused by obesity, diabetes, hyperlipidemia, drugs, or the like. Alcoholic fatty liver occurs when excessive consumption of alcohol promotes fat synthesis in the liver and prevents normal energy metabolism.

The fatty liver disease may be a very serious liver disease, considering the fact that 50% of patients diagnosed with the alcoholic fatty liver disease and 30% of patients diagnosed with the non-alcoholic fatty liver disease develop cirrhosis, beyond the simple accumulation of fat in the liver. In particular, the alcoholic fatty liver disease may progress to chronic liver disease. Among the patients diagnosed with alcoholic fatty liver disease, it has been reported that 10 to 35% of the patients progress to hepatitis and 8 to 20% of the patients progress to cirrhosis. Compared to the patients diagnosed with non-alcoholic fatty liver disease, the patients diagnosed with alcoholic fatty liver disease have more cirrhosis and are more likely to progress to hepatitis, so the alcoholic fatty liver disease is a more serious problem.

Modern people are easily exposed to stress and are placed in an environment in which hepatic function is easily deteriorated along with a decrease in immunity. In addition, as the liver is known as a 'silent organ', it is difficult to notice abnormal symptoms even if a certain level of liver damage occurs. Therefore, preventing deterioration of hepatic function and improving hepatic function are very important in maintaining the overall health of modern people. Accordingly, studies on foods or drugs that can improve hepatic function are being actively conducted.

SUMMARY OF THE INVENTION

In one aspect, the disclosure is to provide a composition for improving hepatic function.

In one aspect, the disclosure provides a composition for improving hepatic function, comprising a green tea-derived *Lactiplantibacillus plantarum* strain; a culture of the strain; a lysate of the strain; an extract of the strains; an extract of the culture; or an extract of the lysate as an active ingredient.

In an exemplary embodiment, the strain may be a *Lactiplantibacillus plantarum* APsulloc 331261 (Accession No.: KCCM11179P) deposited on Mar. 28, 2011 in the Korean Culture Center of Microorganisms under the Budapest Treaty.

In an exemplary embodiment, the improvement of the hepatic function may comprise prevention, alleviation or treatment of fatty liver.

In an exemplary embodiment, the fatty liver may comprise at least one of an alcoholic fatty liver and a non-alcoholic fatty liver.

In an exemplary embodiment, the composition may inhibit fat accumulation in a hepatocyte.

In an exemplary embodiment, the composition may inhibit oxidative stress in a hepatocyte.

In an exemplary embodiment, the active ingredient may be administered at a dosage of 10 to 500 mg/kg/day.

In an exemplary embodiment, the dosage of the green tea-derived *Lactiplantibacillus plantarum* strain by the composition may be $10^5$ to $10^{13}$ CFU/day.

In an exemplary embodiment, the strain may be a non-viable strain.

In an exemplary embodiment, the composition may be administered orally.

In an exemplary embodiment, the composition may be a food composition.

In an exemplary embodiment, the composition may be a pharmaceutical composition.

In one aspect, the composition according to the disclosure is excellent in improving hepatic function without side effects.

In one aspect, the composition according to the disclosure can inhibit fat accumulation in hepatocytes.

In one aspect, the composition according to the disclosure can inhibit oxidative stress in hepatocytes.

DETAILED DESCRIPTION OF THE INVENTION

Figure 1:
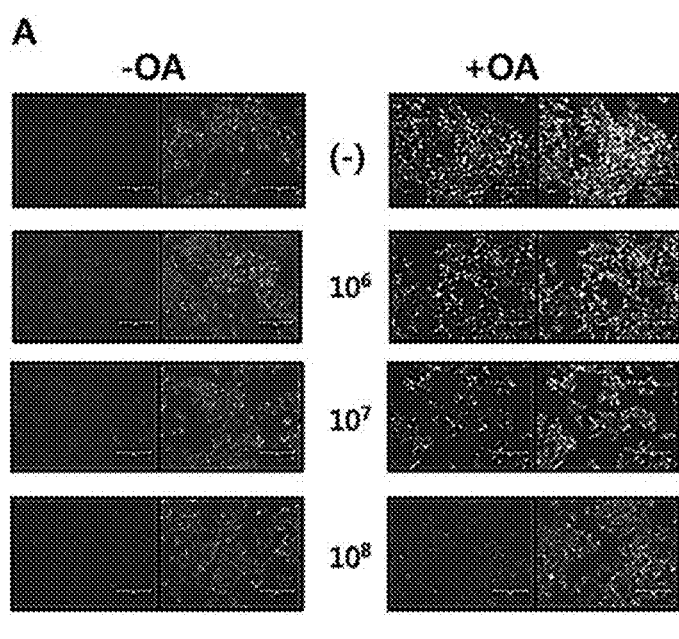
FIG. 1 is a result of measuring the effect of inhibiting fat accumulation due to oleic acid in hepatocytes by a green tea-derived *Lactiplantibacillus plantarum* according to one embodiment of the disclosure.
Figure 1:
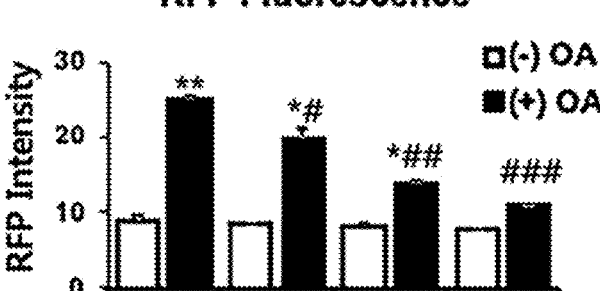

As for terms used in the present specification, general terms widely used at present are selected as much as possible in consideration of their functions in the disclosure, however, they may be different according to intentions of those skilled in the art, precedents, or the emergence of new technology, etc. In addition, terms arbitrarily selected by the applicant may be used in a special case, and the meanings thereof will be described in detail in the corresponding detailed description section. Therefore, the terms used in the disclosure may not be defined by simple names of the terms but by meanings the terms have and contents throughout the disclosure.

Unless defined otherwise, all terms used herein, including technical or scientific terms, have the same meaning as commonly understood by one of ordinary skill in the art to which this invention belongs. Terms that are generally understood may be interpreted as having the same meaning as commonly understood in the context of the relevant art and may not be interpreted in an idealized or overly formal sense unless expressly so defined herein.

Numerical ranges include the numbers defined in the disclosure. All maximum numerical limitations in this specification are expressly written with a lower numerical limitation, including all lower numerical limitations. All minimum numerical limitations given throughout this specification are to be understood as meaning higher numerical limitations, including all higher numerical limitations. All numerical limitations in this specification are to be understood as if they were expressly written to include narrower numerical limitations than those expressly written to include all numerical limitations that are more completely within the broader numerical range.

As used in this disclosure, the terms "comprising," "having," "including," and "containing" are inclusive or open-ended and do not exclude features or method steps that are not further mentioned. The term "or a combination thereof" as used herein refers to all permutations or combination of the plurality of items listed prior to the term. For example, "A, B, C or a combination thereof" refers to A, B, C, AB, AC, BC, or ABC, and further includes at least one of BA, CA, CB, CBA, BCA, ACB, BAC, or CAB where order is important in a particular context. At the same time, is expressly intended to include one or more repeated combinations of items or terms, such as BB, AAA, MB, BBC, AAABCCCC, CBBAAA, CABABB, and the like. It will be understood by those within the art that, in general, the number of items or terms in any combination is not limited, unless the context indicates otherwise.

Exemplary embodiments of the disclosure are described in detail below.

In one aspect, the disclosure provides a composition for improving hepatic function, comprising a green tea-derived *Lactiplantibacillus plantarum* strain; a culture of the strain; a lysate of the strain; an extract of the strains; an extract of the culture; or an extract of the lysate as an active ingredient.

In the specification, "green tea" includes a tea (*Camellia sinensis*), which is an evergreen shrub belonging to the tea family, and the tea may include one or more selected from the group consisting of leaves, flowers, stems, fruits, roots, and root cores of tea plant.

In the specification, the "green tea-derived" may mean that it is separated from tea tree leaves, tea tree flowers, tea tree stems, tea tree fruits, tea tree roots, or nearby soil. For example, it may refer to a *Lactiplantibacillus plantarum* strain cultured and isolated from green tea, which is a tea tree leaf.

In the specification, the "lysate of the strain" may refer to a product obtained by lysing the strain itself either chemically or by applying physical force.

In the specification, the "culture of the strain" may refer to a material containing some or all materials included in the culture medium in which the strain was cultured. For example, it may refer to a material including a metabolite or a secreted product resulting from the culturing of the strain, or a lysate thereof, and the non-viable strain may also be included in the culture.

In the specification, the "extract" may refer to a product obtained by extracting the strain itself, a lysate of the strain, a culture of the strain, a non-viable strain, or a mixture thereof with extraction solvent.

In the specification, the "active ingredient" may refer to an ingredient that alone exhibits the desired activity or that can exhibit the activity in combination with a carrier having no activity by itself.

In the specification, *Lactiplantibacillus plantarum* strain is also called as *Lactobacillus plantarum*. There was taxonomic changes to the genus *Lactobacillus* in 2020, resulting in the renaming of "*Lactobacillus plantarum*" to "*Lactiplantibacillus plantarum*"

In one embodiment, the strain may be *Lactiplantibacillus plantarum* APsulloc 331261 having accession number KCCM11179P. *Lactiplantibacillus plantarum* APsulloc 331261 is the strain isolated from the tea tree as described above, and can have very excellent efficacy in improving hepatic function, such as inhibition of fat accumulation in hepatocytes and oxidative stress in hepatocytes.

In one embodiment, the composition may include 0.000001 to 50% by weight of the active ingredient based on the total weight of the composition. If the content is less than 0.000001% by weight, the effect of improving hepatic function may be insignificant, and if the content is more than 50% by weight, the efficiency of improving hepatic function may be reduced. For example, the composition may include 0.0000001% by weight or more, 0.0000005% by weight or more, 0.0000007% by weight or more, 0.0000009% by weight or more, 0.000001% by weight or more, 0.000002% by weight or more, 0.000004% by weight or more, 0.000006% by weight or more, 0.000008% by weight or more, 0.00001% by weight or more, 0.00003% by weight or more, 0.00005% by weight or more, 0.00007% by weight or more, 0.00009% by weight or more, 0.0001% by weight or more, 0.0003% by weight or more, 0.0005% by weight or more, 0.0007% by weight or more, 0.0009% by weight or more, 0.001% by weight or more, 0.01% by weight or more, 0.1% by weight or more, 1% by weight or more, 3% by weight or more, 5% by weight or more, 7% by weight or more, 9% by weight or more, 10% by weight or more, 13% by weight or more, 15% by weight or more, 17% by weight or more, 19% by weight or more, 21% by weight or more, 23% by weight or more, 25% by weight or more, 27% by weight or more, 29% by weight or more, 30% by weight or more, 50% by weight or less, 49.9% by weight or less, 49.8% by weight or less, 49.7% by weight or less, 49.5% by weight or less, 49% by weight or less, 48.5% by weight or less, 48% by weight or less, 47.5% by weight or less, 47% by weight or less, 46.5% by weight or less, 46% by weight or less, 45.5% by weight or less, 45% by weight or less, 44.5% by weight or less, 44% by weight or less, 43.5% by weight or less, 43% by weight or less, 42.5% by weight or less, 42% by weight or less, 41.5% by weight or less, 41% by weight or less, 40.5% by weight or less, 40% by weight or less, 39% by weight or less, 38% by weight or less, 37% by weight or less, 36% by weight or less, 35% by weight or less, 34% by weight or less, 33% by weight or less, 32% by weight or less, 31% by weight or less, 30% by weight or less, 29% by weight or less, 28% by weight or less, 26% by weight or less, 24% by weight or less, 22% by weight or less, 20% by weight or less, 18% by weight or less, 16% by weight or less, 14% by weight or less, 12% by weight or less, 10% by weight or less, 9% by weight or less, 8% by weight or less, 6% by weight or less, 4% by weight or less, 2% by weight or less, 1% by weight or less, 0.1% by weight or less, 0.09% by weight or less, 0.04% by weight or less, 0.01% by weight or less, 0.006% by weight or less, 0.001% by weight or less, 0.0009% by weight or less, 0.0007% by weight or less, 0.00005% by weight or less, 0.00003% by weight or less, 0.00001% by weight or less, 0.000009% by weight or less, 0.000007% by weight or less, 0.000005% by weight or less, 0.000003% by weight or less, or 0.000001% by weight or less of the active ingredient based on the total weight of the composition, but is not limited thereto.

In one embodiment, the active ingredient of the composition may be administered at a dosage of 10 to 500 mg/kg/day. If the dosage of the active ingredient is less than 10 mg/kg/day, the improvement of hepatic function may be insignificant, and if the dose of the active ingredient exceeds 500 mg/kg/day, the improvement efficiency of hepatic function may be reduced. Specifically, the dose of the active ingredient may be 10 mg/kg/day or more, 11 mg/kg/day or more, 12 mg/kg/day or more, 14 mg/kg/day or more, 16 mg/kg/day or more, 18 mg/kg/day or more, 20 mg/kg/day or more, 22 mg/kg/day or more, 24 mg/kg/day or more, 26 mg/kg/day or more, 28 mg/kg/day or more, 30 mg/kg/day or more, 32 mg/kg/day or more, 34 mg/kg/day or more, 36 mg/kg/day or more, 38 mg/kg/day or more, 40 mg/kg/day or more, 500 mg/kg/day or less, 480 mg/kg/day or less, 460 mg/kg/day or less, 440 mg/kg/day or less, 420 mg/kg/day or less, 400 mg/kg/day or less, 380 mg/kg/day or less, 360 mg/kg/day or less, 340 mg/kg/day or less, 320 mg/kg/day or less, 300 mg/kg/day or less, 280 mg/kg/day or less, 260 mg/kg/day or less, 240 mg/kg/day or less, 220 mg/kg/day or less, 200 mg/kg/day or less, 180 mg/kg/day or less, 160 mg/kg/day or less, 140 mg/kg/day or less, 120 mg/kg/day or less, 100 mg/kg/day or less, 98 mg/kg/day or less, 96 mg/kg/day or less, 94 mg/kg/day or less, 92 mg/kg/day or less, 90 mg/kg/day or less, 88 mg/kg/day or less, 86 mg/kg/day or less, 84 mg/kg/day or less, 82 mg/kg/day or less, 80 mg/kg/day or less, 78 mg/kg/day or less, 76 mg/kg/day or less, 74 mg/kg/day or less, 72 mg/kg/day or less, or 70 mg/kg/day or less, but is not limited thereto.

In one embodiment, the dosage of the green tea-derived *Lactiplantibacillus plantarum* strain by the composition may be $10^5$ to $10^{13}$ CFU/day. If the dosage of the green tea-derived *Lactiplantibacillus plantarum* strain is less than $10^5$ CFU/day, the effect of improving hepatic function may be insignificant, and if the dosage exceeds $10^{13}$ CFU/day, the efficiency of improving hepatic function may be reduced. For example, the dosage of the green tea-derived *Lactiplantibacillus plantarum* strain by the composition may be $1\times10^5$ CFU/day or more, $2\times10^5$ CFU/day or more, $3\times10^5$ CFU/day or more, $4\times10^5$ CFU/day or more, $5\times10^5$ CFU/day or more, $6\times10^5$ CFU/day or more, $7\times10^5$ CFU/day or more, $8\times10^5$ CFU/day or more, $9\times10^5$ CFU/day or more, $1\times10^6$ CFU/day or more, $2\times10^6$ CFU/day or more, $3\times10^6$ CFU/day or more, $4\times10^6$ CFU/day or more, $5\times10^6$ CFU/day or more, $6\times10^6$ CFU/day or more, $7\times10^6$ CFU/day or more, $8\times10^6$ CFU/day or more, $9\times10^6$ CFU/day or more, $1\times10^7$ CFU/day or more, $1\times10^{13}$ CFU/day or less, $9\times10^{12}$ CFU/day or less, $8\times10^{12}$ CFU/day or less, $7\times10^{12}$ CFU/day or less, $6\times10^{12}$ CFU/day or less, $5\times10^{12}$ CFU/day or less, $4\times10^{12}$ CFU/day or less, $3\times10^{12}$ CFU/day or less, $2\times10^{12}$ CFU/day or less, $1\times10^{12}$ CFU/day or less, $9\times10^{11}$ CFU/day or less, $8\times10^{11}$ CFU/day or less, $7\times10^{11}$ CFU/day or less, $6\times10^{11}$ CFU/day or less, $5\times10^{11}$ CFU/day or less, $4\times10^{11}$ CFU/day or less, $3\times10^{11}$ CFU/day or less, $2\times10^{11}$ CFU/day or less, $1\times10^{11}$ CFU/day or less, $9\times10^{10}$ CFU/day or less, $8\times10^{10}$ CFU/day or less, $7\times10^{10}$ CFU/day or less, $6\times10^{10}$ CFU/day or less, $5\times10^{10}$ CFU/day or less, $4\times10^{10}$ CFU/day or less, $3\times10^{10}$ CFU/day or less, $2\times10^{10}$ CFU/day or less, or $1\times10^{10}$ CFU/day or less.

In one embodiment, the improvement of hepatic function may include prevention, alleviation or treatment of fatty liver. The prevention, alleviation or treatment of fatty liver may include preventing, alleviating, or treating fatty liver disease. The fatty liver disease may comprise at least one of the alcoholic fatty liver disease and the non-alcoholic fatty liver disease.

In one embodiment, the composition can inhibit fat accumulation in hepatocytes.

In one embodiment, the composition can inhibit oxidative stress in hepatocytes.

In one embodiment, the strain may be a non-viable bacterium. For example, a green tea-derived *Lactiplantibacillus plantarum* strain, which is a viable bacterium, may be physically or chemically treated to obtain a non-viable green tea-derived *Lactiplantibacillus plantarum* strain. In addition, the green tea-derived *Lactiplantibacillus plantarum* strain, which is a viable bacterium, may be treated with ultrasonic waves, or the green tea-derived *Lactiplantibacillus plantarum* strain, which is a viable bacterium, may be pulverized to obtain a non-viable green tea-derived *Lactiplantibacillus plantarum* strain.

In one embodiment, the composition may be administered orally, but is not necessarily limited thereto.

In one embodiment, the composition may be a food composition. The formulation of the food composition is not particularly limited. The food composition may be formulated into, for example, a tablet, a granule, a pill, a powder, a liquid such as a drink, a caramel, a gel, a bar, a tea bag, or the like. The food composition of each formulation may contain, in addition to the active ingredient, ingredients commonly used in the art that may be selected without difficulty by those skilled in the art depending on the particular formulation or purpose of use, and when a synergistic effect may occur when the additional ingredients are used together.

The food composition according to one embodiment may include various nutrients, vitamins, minerals (electrolytes), flavoring agents such as synthetic flavoring agents and natural flavoring agents, colorants and enhancers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like. In addition, the food compositions according to one embodiment may include flesh of fruit for the preparation of natural fruit juices and fruit juice drinks and vegetable drinks. These ingredients may be used either alone or in combinations thereof. The proportion of these additives is not significantly important, but is generally included within a range of 0 to 50 parts by weight per 100 parts by weight of the composition according to one embodiment.

In one embodiment, the composition may be a pharmaceutical composition. The pharmaceutical composition may be administered orally, parenterally, rectally, topically, transdermally, intravenously, intramuscularly, intraperitoneally, subcutaneously, and the like. The formulation for oral administration may be tablets, pills, soft and hard capsules, granules, powders, fine granules, solutions, emulsions or pellets, but are not limited thereto. The formation for parenteral administration may be solutions, suspensions, emulsions, gels, injections, drops, suppositories, patches or sprays, but are not limited thereto. The formulation may be easily prepared by a typical method in the art, and may further include surfactants, excipients, wettable powders, emulsifying accelerators, suspensions, salts or buffers for controlling osmotic pressure, colorants, spices, stabilizers, antiseptics, preservatives, or other equivalent adjuvants.

In one aspect, the disclosure provides a use of a green tea-derived *Lactiplantibacillus plantarum* strain; a culture of the strain; a lysate of the strain; an extract of the strain; an extract of the culture; or an extract of the lysate for a preparation of a composition for improving hepatic function.

In one aspect, the disclosure provides a method for improving hepatic function comprising administering an effective amount of a composition comprising a green tea-derived *Lactiplantibacillus plantarum* strain; a culture of the strain; a lysate of the strain; an extract of the strain; an extract of the culture; or an extract of the lysate to a subject in need thereof.

In one aspect, the disclosure provides a use of a green tea-derived *Lactiplantibacillus plantarum* strain; a culture of the strain; a lysate of the strain; an extract of the strain; an extract of the culture; or an extract of the lysate for improving hepatic function.

Hereinafter, the disclosure will be described in more detail with reference to the Examples or the like. However, the following examples are for illustrative purposes only to help understand the disclosure and it will be obvious to those skilled in the art that the scope of the disclosure is not limited by them.

[EXAMPLE 1] *LACTIPLANTIBACILLUS PLANTARUM* APSULLOC 331261

1. Culture and Isolation of *Lactiplantibacillus Plantarum* APsulloc 331261

200 g of tea tree leaf was washed 2 times with primarily distilled water to remove impurities. After removing water from the washed tea tree leaf, it was mixed with 8 wt % of salt based on the weight of the tea tree leaf and kept at room temperature for 3 hours. The salted tea tree leaf was mixed with 1000 mL of a 1% fructo-oligosaccharide solution and incubated for 3 days in an incubator at 32° C. After 3 days, it was determined whether the pH of the culture decreased below 5. The culture at pH below 5 was taken and incubated in a Difco Lactobacilli MRS Agar® medium. The incubation was performed for 2 days in a chamber at 32° C. under anaerobic condition and the white colony was taken, so that *Lactiplantibacillus plantarum* APsulloc 331261 was isolated from the tea tree leaf. The *Lactiplantibacillus plantarum* APsulloc 331261 was accredited on Mar. 28, 2011 to the Korean Culture Center of Microorganisms under the Accession No. KCCM11179P.

2. Identification of *Lactiplantibacillus Plantarum* APsulloc 331261

(1) Strain culture

The *Lactiplantibacillus plantarum_APsulloc* 331261 isolated above was streaked on a MRS agar plate, and cultured at 37° C. for 2 days. The obtained single colony was inoculated to MRS broth 10 mL, and then cultured at 37° C. overnight to prepare a *Lactiplantibacillus plantarum* APsulloc 331261 strain culture solution.

(2) Analysis of Sugar Fermentation Pattern

The *Lactiplantibacillus plantarum* APsulloc 331261 strain culture solution prepared as described in (1) was inoculated to MRS broth 10 mL to the concentration of 0.5% and cultured at 37° C. overnight. The culture solution was centrifuged at 8,000 rpm for 5 minutes, supernatant was removed, and then only bacteria were collected. Then, 0.85% saline buffer 2 mL was added to the bacteria and suspended. Later process was conducted by using API 50CHL kit (Biomerieux) according to a manufacturer's protocol. Specific process is as follows. First of all, while gradually adding the strain suspension to API suspension medium 5 mL, the amount of suspension needed to make cloudiness of about McFarland Standard 2 (Biomerieux) was measured. Twice of the measured amount of the suspension was added to API 50CHL medium 10 mL, and then shaken for mixing. The above mixture was added to cupules containing different substrate, one drop of mineral oil was added thereto, and then the mixture was cultured at 37° C. for 2 days to analyze sugar fermentation pattern.

The result of sugar fermentation pattern of the *Lactiplantibacillus plantarum* APsulloc 331261 compared with the *Lactiplantibacillus plantarum* strain (KCTC3108) as a standard strain and the identification result of the of the APsulloc 331261 using the sugar fermentation pattern result are as shown in the following Table 1.

TABLE 1

| | KCTC3108 | | APsulloc 331261 | | | KCTC3108 | | APsulloc 331261 | |
|---|---|---|---|---|---|---|---|---|---|
| Substrate | 24 h | 48 h | 24 h | 48 h | Substrate | 24 h | 48 h | 24 h | 48 h |
| Control | – | – | – | – | Esculin | + | + | + | + |
| Glycerol | – | – | – | – | Salicin | + | + | + | + |
| Erythritol | – | – | – | – | Cellobiose | ? | + | + | + |
| D-arabinose | – | – | – | – | Maltose | + | + | + | + |
| L-arabinose | + | + | + | + | Lactose | + | + | + | + |
| Ribose | + | + | + | + | Melibiose | + | + | + | + |
| D-xylose | – | – | – | – | D-saccharose (Sucrose) | + | + | + | + |
| L-xylose | – | – | – | – | Trehalose | + | + | + | + |
| Adonitol | – | – | – | – | Inulin | – | – | – | – |
| β-methyl-D-xylose | – | – | – | – | Melezitose | + | + | + | + |
| Galactose | + | + | + | + | Raffinose | – | – | + | + |
| Glucose | + | + | + | + | Amidon (Starch) | – | – | – | – |
| Fructose | + | + | + | + | Glycogen | – | – | – | – |
| Mannose | + | + | + | + | Xylitol | – | – | – | – |
| Sorbose | – | – | – | – | Gentiobiose | – | – | + | + |
| Rhamnose | – | – | – | – | D-turanose | + | + | + | + |
| Dulcitol | – | – | – | – | D-lyxose | – | – | – | – |
| Inositol | – | – | – | – | D-tagatose | – | – | – | – |
| Mannitol | + | + | + | + | D-fucose | – | – | – | – |
| Sorbitol | + | + | + | + | L-fucose | – | – | – | – |
| α-methyl-D-mannoside | ? | + | – | – | D-arabitol | ? | – | ? | – |
| α-methyl-D-glucoside | – | – | – | – | L-arabitol | – | – | – | – |
| N-acetyl-glucosamine | + | + | + | + | Gluconic acid | ? | + | ? | + |
| Amygdalin | + | + | + | + | 2-ketogluconate | – | – | – | – |
| Arbutin | + | + | + | + | 5-ketogluconate | – | – | – | – |

+: degradation of substrate,
–: no substrate degradation,
?: unable to determine

TABLE 2

| Strain | Name of species | % Index | T Index |
|---|---|---|---|
| KCTC3108 | *Lactiplantibacillus plantarum* | 99.9 | 0.8 |
| | *Lactiplantibacillus pentosus* | 0.1 | 0.29 |
| APsulloc331261 | *Lactiplantibacillus plantarum* | 99.4 | 0.99 |
| | *Lactiplantibacilluspentosus* | 0.4 | 0.71 |

As can be seen from the above, the APsulloc 331261 shows the consistency (% index) to the *Lactiplantibacillus plantarum* of 99% or more. Accordingly, it is confirmed that this strain is belong to the *Lactiplantibacillus plantarum*. Further, compared with the standard strain (KCTC3108), it can be seen that the APsulloc 331261 is different in use of a-methyl-mannoside and raffinose,

3. Preparation of a Non-Viable *Lactiplantibacillus Plantarum* APsulloc 331261

The cultured *Lactiplantibacillus plantarum* APsulloc 331261 was heated at 100° C. for 15 minutes to be converted to a non-viable form, and then the non-viable cells were centrifuged at 3,000 rpm for 30 minutes to separate the culture medium. The remaining pellets were lyophilized to prepare a non-viable *Lactiplantibacillus plantarum* APsulloc 331261.

[Experimental Example 1] Evaluation of the Efficacy of Inhibiting Fatty Liver

Hepatocyte cell line (HepG2 cell, ATCC) was pretreated with the *Lactiplantibacillus plantarum* APsulloc 331261 of Example 1 at each concentration ($10^6$ to $10^8$ CFU/ml) for 24 hours, followed by oleic acid (OA; 500 µM, Sigma Aldrich) for 72 hours so that the fatty liver was induced. In order to determine the accumulated fat, staining was performed using a Nile-red (Sigma Aldrich) solution, and the result was shown in FIG. 1.

As can be seen in FIG. 1, it was confirmed that treatment with oleic acid increased triglycerides in hepatocytes, but treatment with the green tea-derived *Lactiplantibacillus plantarum* inhibited accumulation of the oleic acid-induced triglycerides in hepatocytes.

In order to examine whether it has the same inhibitory effect on alcohol, another major cause of fatty liver, the cell line was pretreated with the *Lactiplantibacillus plantarum* APsulloc 331261 under the same conditions as above and then treated with ethanol (EtOH; 2 mM, Sigma Aldrich) for 72 hours. In order to determine the accumulated fat, staining was performed using a Nile-red (Sigma Aldrich) solution, and the result was shown in FIG. 2, and cell viability was measured, and the result was shown in FIG. 3.

Figure 2:
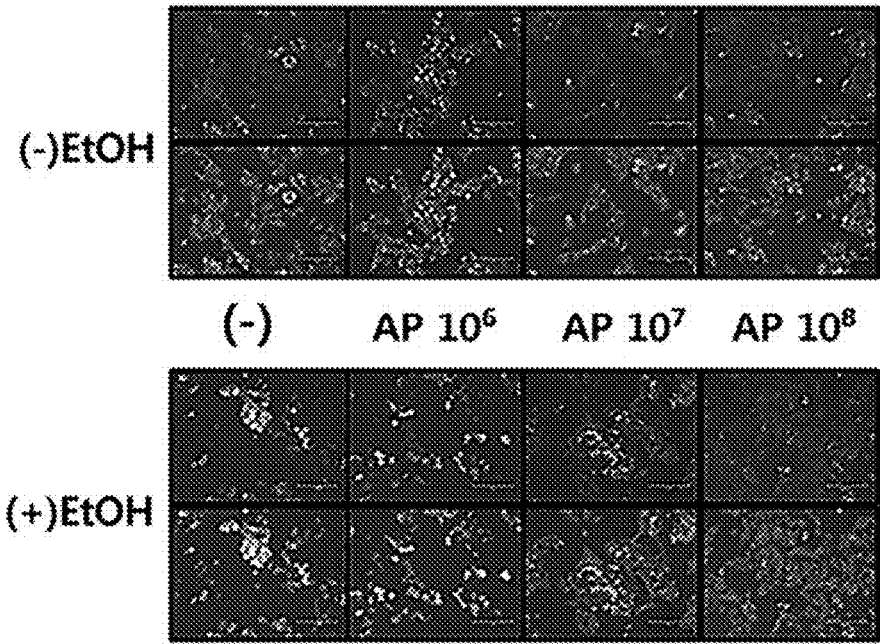
FIG. 2 is a result of measuring the effect of inhibiting fat accumulation due to alcohol in hepatocytes by a green tea-derived *Lactiplantibacillus plantarum* according to one embodiment of the disclosure.
Figure 3:
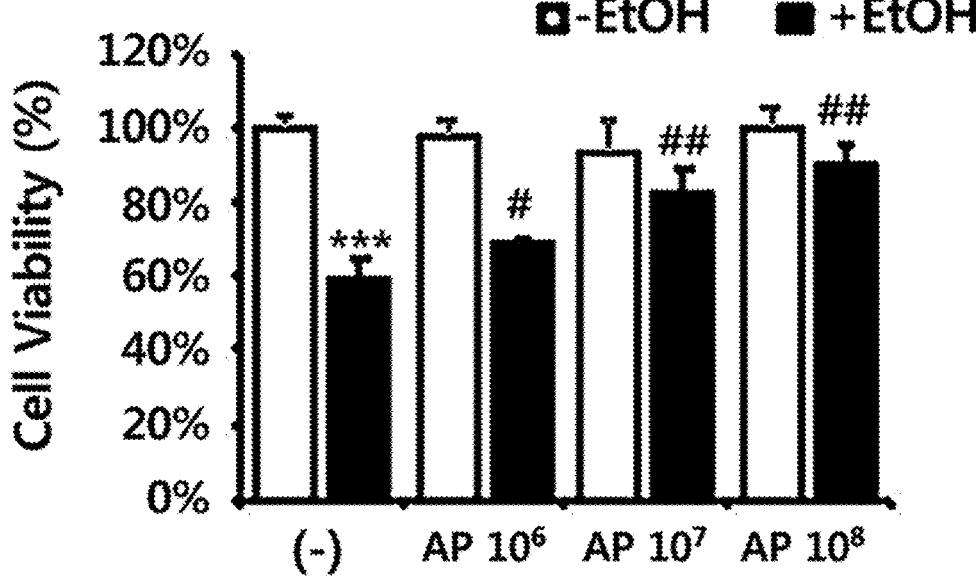
FIG. 3 is a result of measuring the effect of inhibiting alcohol-induced liver damage by a green tea-derived *Lactiplantibacillus plantarum* according to one embodiment of the disclosure.

As can be seen in FIG. 2, it was confirmed that the treatment with ethanol increased the triglycerides in hepa-tocytes, but the treatment with the green tea-derived *Lacti-plantibacillus plantarum* inhibited the accumulation of ethanol-induced triglycerides in hepatocytes. In addition, as shown in FIG. 3, it was found that green tea-derived *Lactiplantibacillus plantarum* inhibited liver damage caused by ethanol. Taken together, it was found that green tea-derived *Lactiplantibacillus plantarum* inhibits fatty liver regardless of the causative agent.

[Experimental Example 2] Assessment of Change of Lipid Metabolism

Fatty liver is an abnormal accumulation of fat in hepatocytes, which is closely related to changes in lipid metabolism. Accordingly, in order to determine whether the green tea-derived *Lactiplantibacillus plantarum* can alleviate fatty liver symptoms by influencing lipid metabolism in hepatocytes, the hepatocyte cell line (HepG2 cell, ATCC) was treated with the *Lactiplantibacillus plantarum* APsulloc 331261 of Example 1 at each concentration ($10^6$ to $10^8$ CFU/ml), and RNAs thereof were isolated using TAKARA MiniBEST Universal RNA Extraction kit (Takara Bio) and RevertAid First Strand cDNA Synthesis kit (Thermo Fisher Scientific) sequentially, and cDNAs were synthesized based on this. Using the CFX96 Touch Real-Time PCR Detection System (Bio-RAD), changes in the expression levels of the genes related to the lipid metabolism were confirmed, and the results were shown in FIGS. 4*a* to 4*c*. The degree of fatty acid oxidation was measured using the Fatty Acid Oxidation Complete Assay Kit (abcam) for measuring the degree of oxidation based on the intracellular oxygen consumption rate, and was shown in FIG. 5.

Figure 4A:
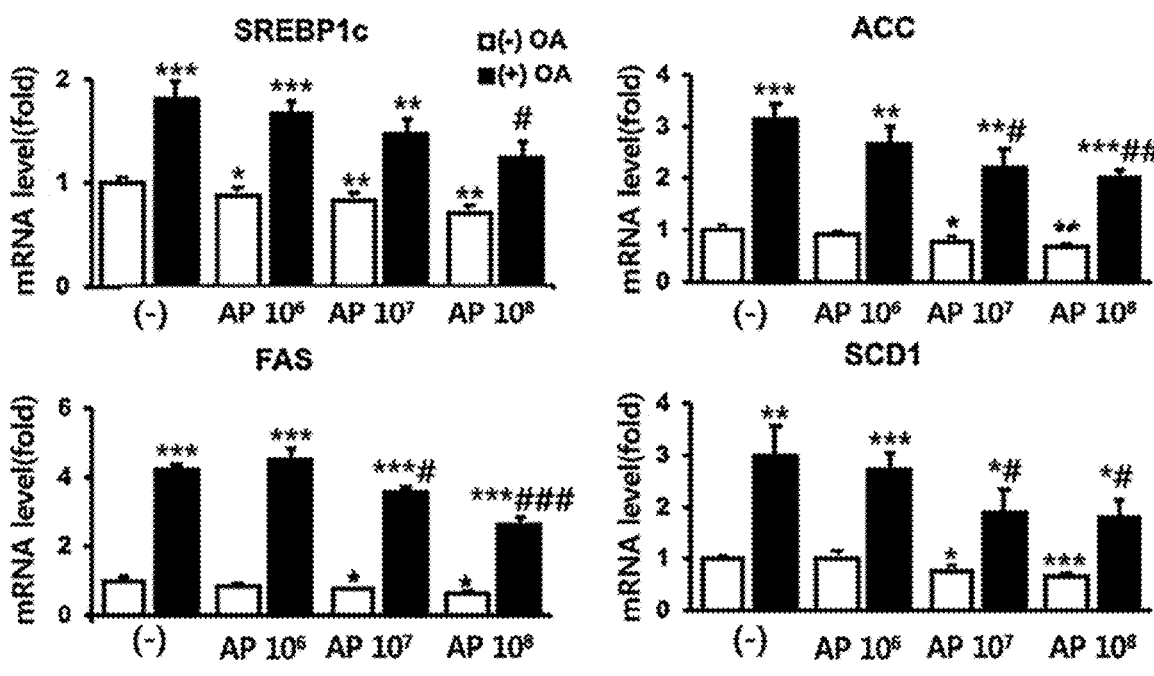
FIG. 4*a* is a result of measuring the expression level change of genes related to fatty acid synthesis by a green tea-derived *Lactiplantibacillus plantarum* according to one embodiment of the disclosure.
Figure 4B:
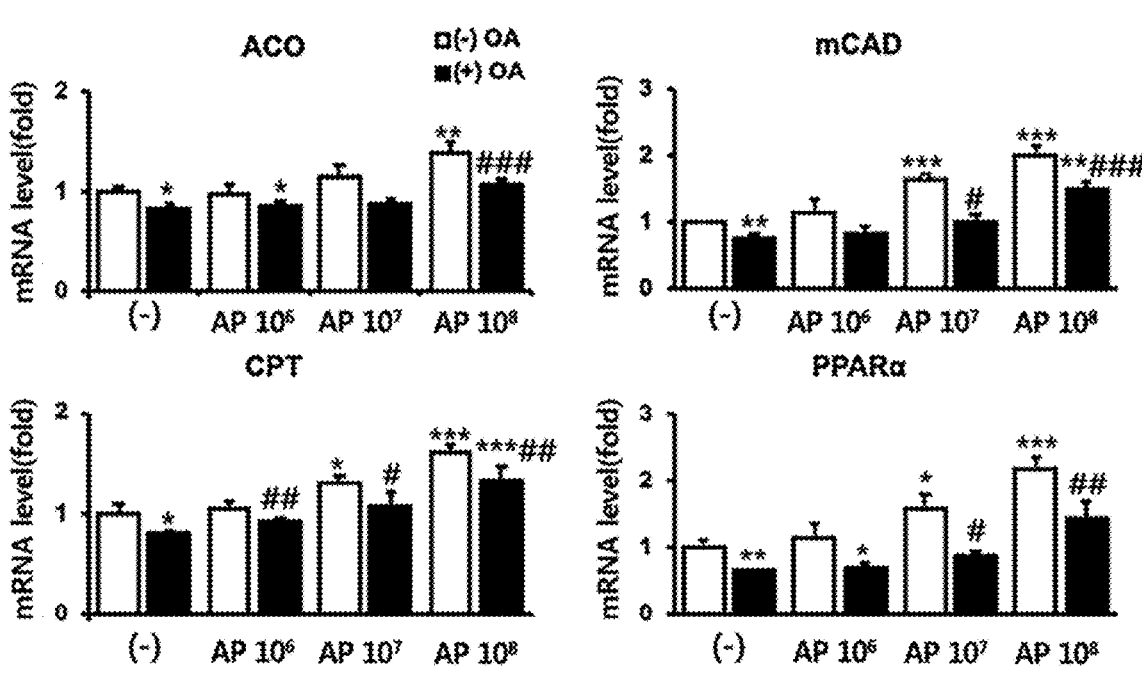
FIG. 4*b* is a result of measuring the expression level change of genes related to fatty acid oxidation by a green tea-derived *Lactiplantibacillus plantarum* according to one embodiment of the present disclosure.
Figure 4C:
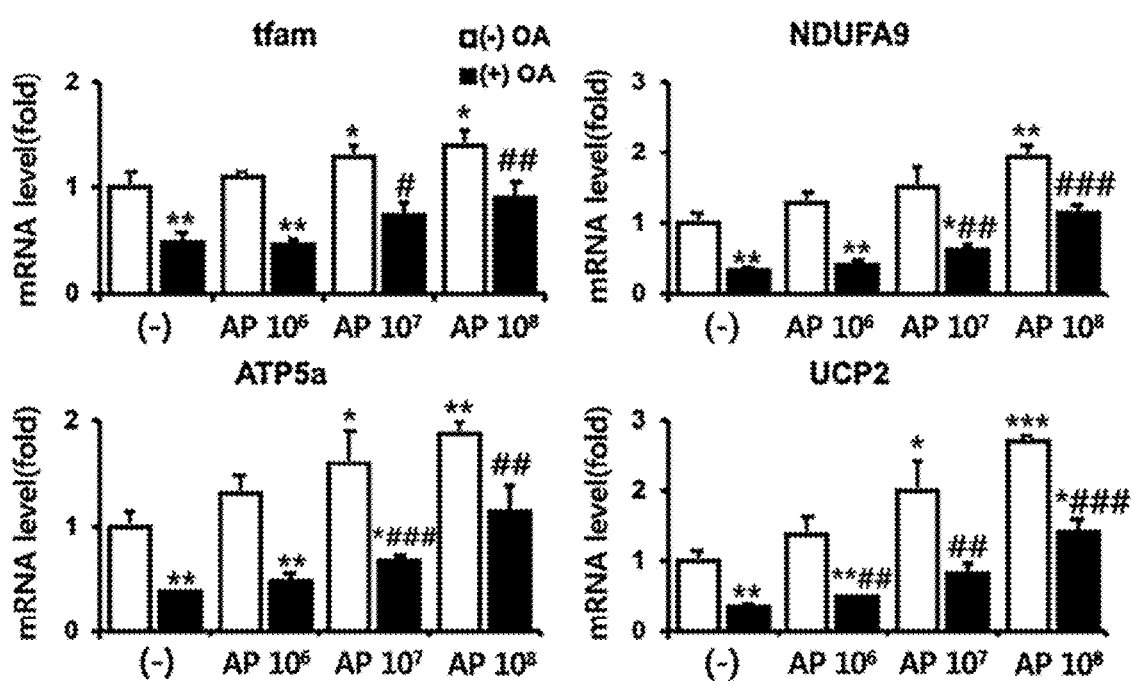
FIG. 4*c* is a result of measuring the expression level change of genes related to mitochondria by a green tea-derived *Lactiplantibacillus plantarum* according to one embodiment of the disclosure.
Figure 5:
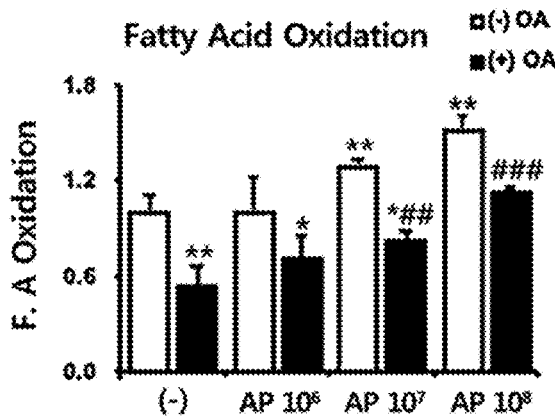
FIG. 5 is a result of measuring the increase in fatty acid oxidation by a green tea-derived *Lactiplantibacillus plantarum* according to one embodiment of the disclosure.

When the green tea-derived *Lactiplantibacillus plantarum* was treated, as shown in FIG. 4*a*, the expression of genes (SREBP1c, ACC, FAS, SCD1) related to the fatty acid synthesis induced by oleic acid was inhibited. Also, as shown in FIG. 4*b*, the expressions of genes (ACO, mCAD, CPT, PPARα) related to the fatty acid oxidation were increased. In addition, as shown in FIG. 4*c*, the green tea-derived *Lactiplantibacillus plantarum* increased the expression of the genes (tfam, NDUFA9, ATP5a, UCP2) related to the production and activity regulation of mitochondria, an organelle that supplies intracellular ATP. As shown in FIG. 5, when the green tea-derived *Lactiplantibacillus plantarum* was treated, the fatty acid oxidation in hepatocytes increased. Through these results, it was found that the green tea-derived *Lactiplantibacillus plantarum* inhibited fat synthesis, promoted fat oxidation, and inhibited fat accumulation in cells by increasing mitochondria to facilitate energy metabolism.

Figure 6:
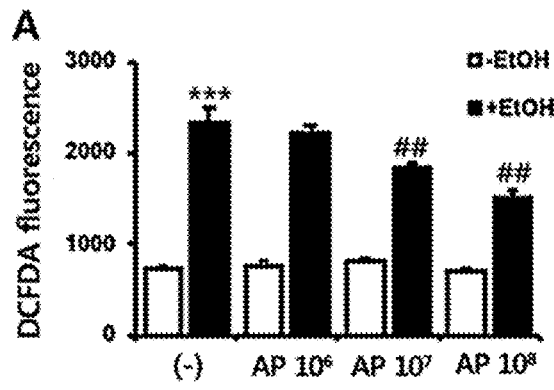
FIG. 6 is a result of measuring the inhibition of oxidative stress in hepatocytes by a green tea-derived *Lactiplantibacillus plantarum* according to an embodiment of the disclosure.
Figure 6:
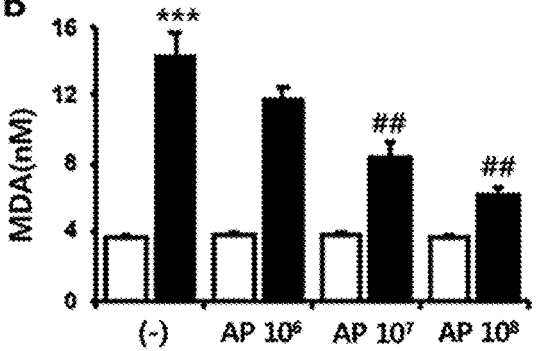

[Experimental Example 3] Evaluation of Oxidative Stress Inhibition Efficacy in Hepatocytes Alcohol generates active oxygen during metabolism, which induces various oxidative stress reactions in cells. Oxidative stress causes abnormal metabolism in cells and induces inflammatory reactions to cause secondary diseases such as liver cirrhosis and liver cancer. Therefore, the inhibition of oxidative stress in hepatocytes is effective in protecting hepatocytes and preventing liver diseases. In order to determine whether the green tea-derived *Lactiplantibacillus plantarum* can inhibit oxidative stress in hepatocytes, the hepatocytes were pretreated with the *Lactiplantibacillus plantarum* APsulloc 331261 of Example 1 for 24 hours and treated with ethanol for 72 hours in the same manner as the ethanol treatment of Experimental Example 1. Then, the amounts of active oxygen and lipid peroxide in cells were measured using DCFDA (Thermo Fisher Scientific) and Malonedialdehyde (MDA) assay kit (Sigma Aldrich), and the results were shown in FIG. 6.

As shown in FIG. 5, it was confirmed that green tea-derived *Lactiplantibacillus plantarum* inhibited the production of active oxygen and lipid peroxides due to the ethanol treatment. Through this, it was found that the green tea-derived *Lactiplantibacillus plantarum* inhibited oxidative stress in hepatocytes.

[Experimental Example 4] Comparison of Fatty Liver Inhibition Efficacies

The fatty liver inhibitory effects of the *Lactiplantibacillus plantarum* APsulloc 331261 and the standard strain *Lactiplantibacillus plantarum* KCTC3108 were compared. Hepatocyte cell lines (HepG2 cells, ATCC) were pretreated with the *Lactiplantibacillus plantarum* APsulloc 331261 and the *Lactiplantibacillus plantarum* KCTC3108 of Example 1 at each concentration ($10^6$ to $10^8$ CFU/ml) for 24 hours, followed by oleic acid (OA; 500 μM, Sigma Aldrich) for 72 hours to induce fatty liver, and after confirming the accumulated fat by staining with Nile-red (Sigma Aldrich) solution, the results were shown in FIG. 7 (in FIG. 7, AP indicates the *Lactiplantibacillus plantarum* APsulloc 331261, KC indicates the *Lactiplantibacillus plantarum* KCTC3108).

Figure 7:
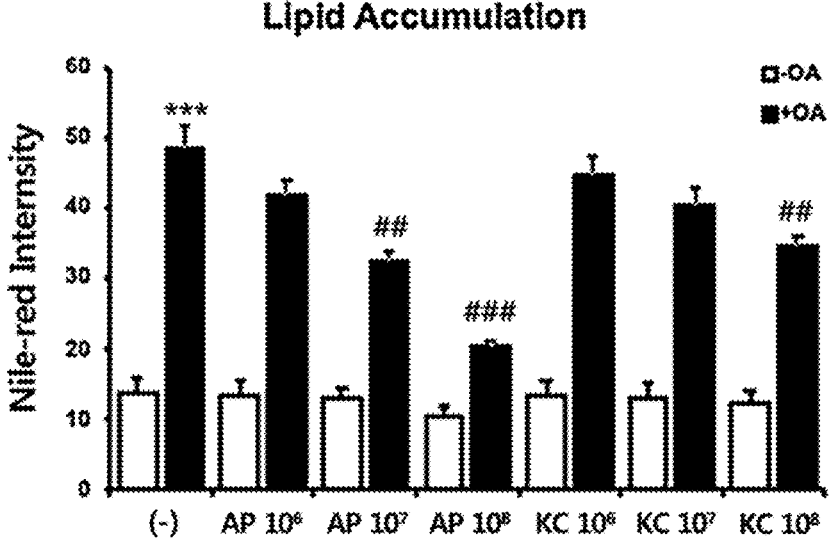
FIG. 7 is a result of measuring the fat accumulation inhibitory effect in hepatocytes of a green tea-derived *Lactiplantibacillus plantarum* according to one embodiment of the disclosure.

As shown in the results of FIG. 7, it can be seen that $10^7$ CFU/ml of the *Lactiplantibacillus plantarum* APsulloc 331261 is superior to $10^8$ CFU/ml of the *Lactiplantibacillus plantarum* KCTC3108 in inhibiting accumulation of triglycerides in hepatocytes. From this, it was confirmed that, compared to the *Lactiplantibacillus plantarum* KCTC3108, the *Lactiplantibacillus plantarum* APsulloc 331261 significantly inhibited the accumulation of triglycerides due to the oleic acid in the hepatocytes.

[Formulation Example 1] Tablet

After mixing $10^9$ to $10^{10}$ CFU of the green tea-derived *Lactiplantibacillus plantarum* (Example 1) according to an embodiment of the disclosure, 400 mg of lactose, 400 mg of corn starch, and 2 mg of magnesium stearate, tablets were prepared by tableting the mixture according to a commonly employed method for preparing tablets. The specific composition was shown in Table 3 below.

TABLE 3

| Ingredient | Content |
| --- | --- |
| Green tea-derived *Lactiplantibacillus plantarum* (Example 1) | $10^9$-$10^{10}$ CFU |
| Lactose | 400 mg |
| Corn starch | 400 mg |
| Magnesium stearate | 2 mg |

[Formulation Example 2] Capsule $10^9$-$10^{10}$ CFU of the green tea-derived *Lactiplantibacillus plantarum* (Example 1) according to an embodiment of the disclosure, 220 mg of soybean oil, 2 mg of palm oil, 8 mg of hydrogenated vegetable oil, 4 mg of yellow wax, and 6 mg of lecithin were mixed, and a capsule was prepared by filling the mixture into one capsule according to a commonly employed method for preparing capsules. The specific composition was shown in Table 4 below.

TABLE 4

| Ingredient | Content |
| --- | --- |
| Green tea-derived *Lactiplantibacillus plantarum* (Example 1) | $10^9$-$10^{10}$ CFU |
| Soybean oil | 220 mg |
| Palm oil | 2 mg |
| Hydrogenated vegetable oil | 8 mg |
| Yellow wax | 4 mg |
| Lecithin | 6 mg |

[Formulation Example 3] Granule $10^9$ to $10^{10}$ CFU of the green tea-derived *Lactiplantibacillus plantarum* (Example 1) according to an embodiment of the disclosure, 250 mg of anhydrous crystalline glucose, and 550 mg of starch were mixed, granulated using a fluidized-bed granulator and then filled in a pouch to prepare granules.

[Formulation Example 4] Powder $10^9$ to $10^{10}$ CFU of the green tea-derived *Lactiplantibacillus plantarum* (Example 1) according to an embodiment of the disclosure, 500 mg of lactose, and 500 mg of corn starch were mixed and filled in an air-tight pack to prepare powders.

[Formulation Example 5] Heath Functional Food

A health functional food was prepared according to a commonly employed method with the composition described in Table 5.

TABLE 5

| Ingredient | Content |
| --- | --- |
| Green tea-derived *Lactiplantibacillus plantarum* (Example 1) | $10^9$-$10^{10}$ CFU |
| Vitamin A acetate | 70 ug |
| Vitamin E | 1 mg |
| Vitamin B1 | 0.13 mg |
| Vitamin B2 | 0.15 mg |
| Vitamin B6 | 0.5 mg |
| Vitamin B12 | 0.2 ug |
| Vitamin C | 10 mg |
| Biotin | 10 ug |
| Nicotinamide | 1.7 mg |
| Folic acid | 50 ug |
| Calcium pantothenate | 0.5 mg |

[Formulation Example 6] Drink

After mixing $10^9$ to $10^{10}$ CFU of the green tea-derived *Lactiplantibacillus plantarum* (Example 1) according to an embodiment of the disclosure, 1000 mg of citric acid, 15 g of oligosaccharide, and 1 g of taurine, 190 ml of purified water was added to fill each bottle with 200 ml. After filling the bottle, sterilization was performed at 130° C. for 4 to 5 seconds to prepare a drink.

The disclosure is further illustrated by the following embodiments, which do not limit the scope of the claims.

Embodiment 1. A method for improving hepatic function, comprising administering an effective amount of a composition comprising a green tea-derived *Lactiplantibacillus plantarum* strain; a culture of the strain; a lysate of the strain; an extract of the strain; an extract of the culture; or an extract of the lysate to a subject in need thereof.

Embodiment 2. The method of Embodiment 1, wherein the strain is a *Lactiplantibacillus plantarum* APsulloc 331261 (Accession No.: KCCM11179P).

Embodiment 3. The method of Embodiment 1 or 2, wherein the improvement of the hepatic function comprises prevention or alleviation of fatty liver.

Embodiment 4. The method of any of Embodiments 1 to 3, wherein the fatty liver comprises at least one of an alcoholic fatty liver and a non-alcoholic fatty liver.

Embodiment 5. The method of any of Embodiments 1 to 4, wherein the subject is in need of inhibiting fat accumulation in a hepatocyte.

Embodiment 6. The method of any of Embodiments 1 to 5, wherein the subject is in need of inhibiting oxidative stress in a hepatocyte.

Embodiment 7. The method of any of Embodiments 1 to 6, wherein the active ingredient is administered at a dosage of 10 to 500 mg/kg/day.

Embodiment 8. The method of any of Embodiments 1 to 7, wherein the composition comprises the active ingredient in 0.000001 to 50% by weight based on a total weight of the composition.

Embodiment 9. The method of any of Embodiments 1 to 8, wherein the composition is administered orally.

Embodiment 10. The method of any of Embodiments 1 to 9, wherein the composition is a food composition.

Embodiment 11. The method of any of Embodiments 1 to 9, wherein the composition is a pharmaceutical composition.

[ Accession No. ]

Depository Institution Name: Korean Culture Center of Microorganisms

Accession No.: KCCM11179P

Deposition Date: Mar. 28, 2011

What is claimed is:

1. A method for improving hepatic function, comprising administering an effective amount of a composition comprising a green tea-derived *Lactiplantibacillus plantarum* APsulloc 331261 strain (Accession No.: KCCM11179P); or a lysate of the strain to a subject in need thereof, wherein the improvement of the hepatic function comprises at least one of: alleviating or treating fatty liver; inhibiting fat accumulation in a hepatocyte; and inhibiting oxidative stress in a hepatocyte.

2. The method of claim 1, wherein the fatty liver comprises at least one of an alcoholic fatty liver and a non-alcoholic fatty liver.

3. The method of claim 1, wherein the strain is a non-viable strain.

4. The method of claim 1, wherein the composition is administered orally.

5. The method of claim 1, wherein the composition is a food composition.

6. The method of claim 1, wherein the composition is a pharmaceutical composition.

* * * * *